United States Patent
Davis et al.

[11] Patent Number: 6,110,153
[45] Date of Patent: Aug. 29, 2000

[54] INFUSION DEVICE WITH OPTICAL SENSOR

[75] Inventors: David L. Davis; Robert E. Brasier; Richard F. Hatch, all of San Diego, Calif.

[73] Assignee: ALARIS Medical Systems, Inc., San Diego, Calif.

[21] Appl. No.: 09/211,223

[22] Filed: Dec. 14, 1998

Related U.S. Application Data

[63] Continuation of application No. 08/686,757, Jul. 25, 1996, Pat. No. 5,853,386.

[51] Int. Cl.[7] .................................................... A61M 5/00
[52] U.S. Cl. ............................... 604/245; 604/31; 604/65
[58] Field of Search ............................. 604/65, 67, 151, 604/153, 154, 131, 122, 123; 128/DIG. 12, DIG. 13; 250/577, 574

[56] References Cited

U.S. PATENT DOCUMENTS

| | | |
|---|---|---|
| T961,004 | 8/1977 | Horton . |
| 2,350,712 | 6/1944 | Barsties . |
| 2,383,347 | 8/1945 | Silge . |
| 2,968,804 | 1/1961 | Buffington . |
| 3,120,125 | 2/1964 | Vasel . |
| 3,199,511 | 8/1965 | Kulick . |
| 3,555,286 | 1/1971 | Cote . |
| 3,731,679 | 5/1973 | Wilhelmson et al. . |
| 3,777,165 | 12/1973 | Bryant et al. . |
| 3,811,800 | 5/1974 | Shill . |
| 3,884,228 | 5/1975 | Hahn . |
| 3,888,239 | 6/1975 | Rubinstein . |
| 3,901,231 | 8/1975 | Olson . |
| 3,985,133 | 10/1976 | Jenkins et al. . |
| 4,037,598 | 7/1977 | Georgi . |
| 4,080,967 | 3/1978 | O'Leary . |
| 4,094,318 | 6/1978 | Burke et al. . |
| 4,126,132 | 11/1978 | Portner et al. . |
| 4,131,399 | 12/1978 | Calvet . |
| 4,137,913 | 2/1979 | Georgi . |
| 4,155,362 | 5/1979 | Jess . |
| 4,184,815 | 1/1980 | Casson et al. . |
| 4,187,057 | 2/1980 | Xanthopoulos . |
| 4,191,184 | 3/1980 | Carlisle . |
| 4,210,138 | 7/1980 | Jess et al. . |
| 4,217,993 | 8/1980 | Jess et al. . |
| 4,231,366 | 11/1980 | Schael . |
| 4,256,437 | 3/1981 | Brown . |
| 4,265,240 | 5/1981 | Jenkins . |
| 4,277,226 | 7/1981 | Archibald . |
| 4,280,136 | 7/1981 | Kashima et al. . |
| 4,311,377 | 1/1982 | Matteson . |
| 4,319,568 | 3/1982 | Tregoning . |

(List continued on next page.)

FOREIGN PATENT DOCUMENTS

| | | |
|---|---|---|
| 0078645A1 | 5/1993 | European Pat. Off. . |
| 551088 | 7/1993 | European Pat. Off. . |
| 2262452 | 6/1993 | United Kingdom . |
| WO84/04685 | 12/1984 | WIPO . |
| WO87/07161 | 12/1987 | WIPO . |

*Primary Examiner*—Ronald Stright
*Assistant Examiner*—Jeremy Thissell
*Attorney, Agent, or Firm*—Fulwider Patton Lee & Utecht, LLP

[57] ABSTRACT

An infusion device with a disposable administration set which is inexpensive to manufacture. In the preferred embodiment of the present invention the disposable administration set has a plurality of elongated cam followers connected to a plate assembly, wherein the cam followers are displace in a predetermined sequence and forced against a delivery tube by cam means driven by rotary drive means. The device also includes an optical occlusion sensor which is synchronized to operate in phase with the movement of the cam followers to measure pressure within the delivery tube at one pump phase, thereby sensing downstream occlusions, and to measure vacuum within the delivery tube at a second pump phase, thereby sensing upstream occlusions. The occlusion sensor is optical, and measures the degree of total internal reflection at the interface of the tube and the plate assembly, occlusion in the tubing.

20 Claims, 10 Drawing Sheets

U.S. PATENT DOCUMENTS

| | | |
|---|---|---|
| 4,332,246 | 6/1982 | Thomson . |
| 4,344,429 | 8/1982 | Gupton et al. . |
| 4,358,202 | 11/1982 | Puffer et al. . |
| 4,373,525 | 2/1983 | Kobayashi . |
| 4,373,527 | 2/1983 | Fischell . |
| 4,382,753 | 5/1983 | Archibald . |
| 4,384,578 | 5/1983 | Winkler . |
| 4,385,958 | 5/1983 | Long . |
| 4,391,600 | 7/1983 | Archibald . |
| 4,396,385 | 8/1983 | Kelly et al. . |
| 4,397,642 | 8/1983 | Lamadrid . |
| 4,410,322 | 10/1983 | Archibald . |
| 4,416,541 | 11/1983 | Studer . |
| 4,443,216 | 4/1984 | Chappell . |
| 4,457,751 | 7/1984 | Rodler . |
| 4,460,355 | 7/1984 | Layman . |
| 4,468,222 | 8/1984 | Lundquist . |
| 4,544,369 | 10/1985 | Skakoon et al. . |
| 4,555,133 | 11/1985 | Zegers de Beyl et al. . |
| 4,557,725 | 12/1985 | Heyne et al. . |
| 4,559,038 | 12/1985 | Berg et al. . |
| 4,559,044 | 12/1985 | Robinson et al. . |
| 4,559,454 | 12/1985 | Kramer . |
| 4,564,542 | 1/1986 | Berg . |
| 4,565,542 | 1/1986 | Berg . |
| 4,597,754 | 7/1986 | Thill et al. . |
| 4,601,702 | 7/1986 | Hudson . |
| 4,617,014 | 10/1986 | Cannon et al. . |
| 4,627,835 | 12/1986 | Fenton, Jr. . |
| 4,650,469 | 3/1987 | Berg et al. . |
| 4,652,260 | 3/1987 | Fenton, Jr. et al. . |
| 4,657,486 | 4/1987 | Stempfle et al. . |
| 4,657,490 | 4/1987 | Abbott . |
| 4,671,792 | 6/1987 | Borsanyi . |
| 4,681,566 | 7/1987 | Fenton, Jr. et al. . |
| 4,731,058 | 3/1988 | Doan . |
| 4,756,706 | 7/1988 | Kerns et al. . |
| 4,762,518 | 8/1988 | Kreinick ................... 604/245 |
| 4,775,368 | 10/1988 | Iwatschenko . |
| 4,790,816 | 12/1988 | Sundblom et al. . |
| 4,799,381 | 1/1989 | Tromp . |
| 4,808,167 | 2/1989 | Mann et al. . |
| 4,818,186 | 4/1989 | Pastrone et al. . |
| 4,838,856 | 6/1989 | Mulreany et al. . |
| 4,838,857 | 6/1989 | Stowe et al. . |
| 4,840,542 | 6/1989 | Abbott . |
| 4,842,584 | 6/1989 | Pastrone . |
| 4,847,990 | 7/1989 | Patrick . |
| 4,850,807 | 7/1989 | Frantz . |
| 4,856,339 | 8/1989 | Williams . |
| 4,863,425 | 9/1989 | Slate et al. . |
| 4,878,896 | 11/1989 | Garrison et al. . |
| 4,927,411 | 5/1990 | Pastrone et al. . |
| 4,943,279 | 7/1990 | Samiotes et al. . |
| 4,950,244 | 8/1990 | Fellingham et al. . |
| 4,961,533 | 10/1990 | Teller et al. . |
| 4,978,335 | 12/1990 | Arthur, III . |
| 5,017,059 | 5/1991 | Davis . |
| 5,029,621 | 7/1991 | Lewis . |
| 5,034,004 | 7/1991 | Crankshaw . |
| 5,047,014 | 9/1991 | Mosebach et al. . |
| 5,062,774 | 11/1991 | Kramer et al. . |
| 5,074,756 | 12/1991 | Davis . |
| 5,078,683 | 1/1992 | Sancoff et al. . |
| 5,082,014 | 1/1992 | Olichney . |
| 5,083,862 | 1/1992 | Rusnak ................... 250/574 |
| 5,092,749 | 3/1992 | Meijer . |
| 5,096,385 | 3/1992 | Georgi et al. . |
| 5,098,262 | 3/1992 | Wecker et al. . |
| 5,098,409 | 3/1992 | Stock . |
| 5,103,211 | 4/1992 | Daoud et al. ................... 604/67 |
| 5,104,374 | 4/1992 | Blahko et al. . |
| 5,111,234 | 5/1992 | Taniguchi et al. . |
| 5,115,223 | 5/1992 | Moody . |
| 5,122,820 | 6/1992 | Pagano et al. . |
| 5,124,744 | 6/1992 | Ogura et al. . |
| 5,124,802 | 6/1992 | Ito et al. . |
| 5,207,642 | 5/1993 | Orkin et al. . |
| 5,211,626 | 5/1993 | Frank et al. . |
| 5,217,355 | 6/1993 | Hyman et al. . |
| 5,219,327 | 6/1993 | Okada . |
| 5,221,268 | 6/1993 | Barion et al. . |
| 5,244,463 | 9/1993 | Cordner, Jr. et al. . |
| 5,246,347 | 9/1993 | Davis ................... 604/67 |
| 5,267,980 | 12/1993 | Dir, Jr. et al. . |
| 5,290,238 | 3/1994 | Classey et al. . |
| 5,317,505 | 5/1994 | Coutre et al. . |
| 5,320,503 | 6/1994 | Davis . |
| 5,431,627 | 7/1995 | Pastrone et al. . |
| 5,445,622 | 8/1995 | Brown ................... 604/65 |
| 5,531,697 | 7/1996 | Olsen et al. . |
| 5,531,698 | 7/1996 | Olsen . |
| 5,826,223 | 10/1998 | Butterfield . |
| 5,827,223 | 10/1998 | Butterfield ................... 604/67 |
| 5,853,386 | 12/1998 | Davis et al. ................... 604/67 |

# INFUSION DEVICE WITH OPTICAL SENSOR

This is a continuation of application Ser. No. 08/686,757 filed on Jul. 25, 1996, "Infusion Device with Disposable Elements" to Davis et al. now having U.S. Pat. No. 5,853,386.

BACKGROUND OF THE INVENTION

1. General Background

This invention relates generally to a medication infusion device for administering fluid to patients and more particularly to an improved, ambulatory infusion device with a disposable administration set which is inexpensive to manufacture, convenient to operate and which ensues fluid delivery at a consistent and uniform rate. More specifically, this invention relates to an occlusion detection system for sensing a blockage in either a supply tube which provides medication to such an ambulatory infusion device or an outlet tube which provides medication from such an infusion device to a patient.

2. Description of the Prior Art

As a result of the ongoing need for improved health care, there is a continuous effort to improve the administration of intravenous fluid to patients. As is well known, medication dispensers and infusion devices are used for infusion of predetermined amounts of medication into the body of a patient. Various types of medication dispensers employing different techniques for a variety of applications are known to exist.

In many cases it is of critical importance to provide precisely controlled and consistent flow rates of intravenous fluid to patients. This need for more controlled IV flow rates is only partially fulfilled by prior art displacement pumps. Specifically, particularly when such pumps are intended for ambulatory use by a patient beyond the vicinity of a hospital or other health care facility, the occurrence of an occlusion in the pump's medication supply tube or output tube may endanger the patient without warning. If, for example, the supply reservoir is empty, or the supply tube becomes kinked, pinched or otherwise blocked, the supply of medication to the patient will cease. As the continued supply of some medications is necessary to sustain the patient or remedy the patient's condition, cessation of supply may even be life threatening. Yet, with most ambulatory pumps, such an occlusion would go unnoticed unless the patient is extraordinarily vigilant.

Similarly, if the needle or catheter which supplies the pump's output to the patient becomes blocked, or the outlet tubing from the pump becomes kinked or blocked, flow of medication to the patient will cease. Furthermore, with such blockage, it may be possible for dangerously high pressures to build within the outlet tube. As this tube is resilient, it may expand with the increased pressure, storing a significant volume of medication. If the rising pressure finally overcomes the blockage, the stored, pressurized medication may be supplied in a surge to the patient, overdosing and possibly endangering the patient.

As is well known, disposable equipment for medical applications is desirable so as to maintain a germ-free environment to prevent the transfer of infection especially where cost prohibits cleaning and sterilization after each use. Disposable elements, especially in an ambulatory infusion environment, must be low in cost, since clinical application of disposable administration sets requires that the administration sets be regularly replaced. Typically, such sets are replaced every 24 to 48 hours, and seldom remain in use longer than one week. This frequent replacement interval should ideally be fulfilled by an inexpensively molded, disposable, mechanism which would normally not last the years of service life expected from the pump itself. To be practical, an occlusion detection system must be able to reliably operate with such disposable administration sets. In the prior art, occlusion sensors have typically mechanically sensed the tubing of the administration set. Thus, such systems required a highly precise, repeatable positioning of the occlusion sensor against each new administration set. This requirement subjected prior art sensors to frequent failure and maintenance problems.

Furthermore, it is desirable to have a disposable administration set which is easy to load and unload to minimize operator errors. These factors can be very important in a clinical situation when a few extra seconds may be critical to a patient's life. Typically, prior art devices require several steps to accomplish the task of loading and unloading, particularly where a tube sensor must be placed against the administration set to detect occlusions.

Some prior art devices incorporate a pressure transducer and diaphragm assembly to monitor fluid pressure as an indication of occlusion. Such an occlusion detection technique is undesirable in view of the complexities and cost involved.

Still other prior art devices use strain gages to measure the diameter of the supply tube as a means of sensing occlusions. For example, it is known to sense the diameter of a supply tube with a strain gage to detect upstream or supply occlusions. Thus, upon the occurrence of an occlusions in the supply tube, or an empty supply bag or vessel, a vacuum will be drawn in the supply tube by the continued operation of the pump. Because the supply tube is formed of resilient material, this vacuum will slightly reduce the diameter of the tube. A strain gage mounted against the outside wall of the tube senses the diameter reduction, and activates an occlusion alarm. Repeatedly placing the disposable tubing accurately against such a strain gage is difficult and makes such systems less reliable than would be desirable.

In a similar fashion, it is known to sense the diameter of the outlet tube to monitor downstream occlusions, such as a blocked needle or obstructed tubing connection. Here, the prior art devices use stain gages to sense the diameter increase in the outlet tube caused by increased pressure which the blockage creates, so that an alarm may be activated. These sensors are subject to the same weaknesses described above.

SUMMARY OF THE INVENTION

Briefly stated, the present invention is an improved occlusion sensing system for an ambulatory infusion device having a disposable administration set. The occlusion sensor is relatively insensitive to mechanical misalignment of the disposable administration set in the pump, is inexpensive to manufacture and provides reliable, consistent protection from both upstream (supply) and downstream (patient output) occlusions.

The present invention utilizes two pumping cams and two pumping cam followers, which function such that, at any point in time, one of the two pumping cams is always pumping. The two pumping cams comprise a primary pumping cam associated with an upstream segment of the delivery tube and a secondary pumping cam associated with a downstream segment of the delivery tube. The primary pumping cam is wider than the secondary pumping cam, so that it can displace sufficient fluid during its pumping stroke to deliver fluid extent to the pump and at the same time deliver fluid to the section of the tubing beneath the secondary pumping cam to allow it to fill. The secondary pumping cam is narrower, since it only needs to deliver fluid external to the pump. The present invention additionally utilizes pinching cams and pinching cam followers, which open and close the delivery tube to allow the pumping action to function properly. The pinching cams comprise an inlet pinching cam associated with the upstream segment of the tube and an outlet pinching cam associated with the downstream segment of the tube. Thus the pumping cam followers, acted upon by the pumping cams, control the rate of fluid flow, while the pinching cam followers acted upon by the pinching cams, operate as valves for the pump. Such a configuration allows one segment of the delivery tube to fill with fluid while another segment of the delivery tube is pumping, thus providing a continuous and uniform fluid flow.

In still another feature of the present invention the disposable administration set of the infusion device is less prone to operator loading errors. This is accomplished through a reduced number of required operations and a reduction in the complexity of the operations. This is facilitated by providing channels extending along the length of the walls of a housing structure of the infusion device. These channels slidingly receive the disposable administration set in a simple, single insertion step. Additionally, since the disposable administration set includes the delivery tube retainer plate and cam followers, the position of the delivery tube relative to the tubing retainer plate and cam followers is established in a manufacturing operation which can be closely controlled. Assemblers are not under the stress of a clinical situation and they specialize in the proper assembly of the disposable administration set. Good manufacturing procedures provide additional checking systems to insure that the tubing is properly loaded and that the administration set properly assembled. These practices are not possible in a clinical environment.

The set loading and retaining channels allow precise positioning of the tubing, followers, and pressure plate without any adjustments or complicated, bulky, or expensive mechanisms. The disposable administration set results in an overall fluid delivery system which is small, lightweight, and ambulatory.

The disposable administration set includes a channel segment which is slightly narrower than the outside diameter of the tubing. Consequently, when the tubing is positioned within this channel at the time of manufacture, a narrow portion of the tube wall will be flattened against the wall of the channel of the administration set. This narrow portion forms a contact line with the channel wall having a highly predictable line width. A source of illumination is directed at the channel wall, and a photodetector is used to measure the width of this contact line. If pressure within the tube causes the tube's diameter to increase, the contact line width will increase. Likewise, if a vacuum is drawn within the tube, so that the diameter of the tube decreases, the contact line width will decrease. In fact, the contact line may disappear altogether if contact between the channel wall and the tube ceases.

This channel segment is placed between the two pinching cam follower locations in the pump. Thus, when the upstream pinching cam pinches the upstream follower against the tube, and the downstream pinching cam follower is raised away from the tube, the tubing in this channel segment is subjected to the output pressure of the pump. When the downstream pinching cam pinches the downstream follower against the delivery tube, and the upstream pinching cam follower is raised away from the tube, the tubing in this channel segment is subjected to the inlet pressure or vacuum of the pump. By synchronizing the measurement of the contact line width with the rotation of the cam, both the upstream and downs pressure may be sensed. This permits a single sensor to monitor for both upstream (supply) and downstream (outlet to patient) occlusions. The use of a single sensing mechanism for both upstream and downstream occlusion sensing simplifies the pump construction, reduces the cost of the system, and increases overall reliability.

In order to measure the contact line width, a light source, such as a light emitting diode (LED) is positioned on the outside of the channel wall at the channel segment. The channel wall is transparent, and the light from the LED thus illuminates the region of contact between the tubing and the channel segment wall. If the light is introduced at an angle relative to the plane of the channel segment wall, total internal reflection will occur at the channel segment wall when the tubing does not contact the wall, i.e., when the difference between the index of refraction of the channel wall and surrounding air is relatively high. When, however, the tubing contacts the channel wall, because the tubing has a higher index of refraction than air, the difference between the refractive indexes of the wall and the tubing is such as to prohibit total internal reflection at the channel wall.

A photodetector is placed at the channel wall, and directed toward the contact line. When total internal reflection occurs, the detector is illuminated. When no total internal reflection occurs, the detector is not illuminated. As the contact line width increases, the degree of total internal reflection is altered, and the amount of light at the photodetector changes. By measuring the output from the photodetector, the pumping system can determine the extent of pressure or vacuum in the tube at the channel segment.

If, during a time when the upstream pinching cam releases the upstream follower from the tubing, the output of the photodetector increases, indicating increased total internal reflection caused by a narrowing of the contact line due to vacuum in the tubing, an upstream occlusion alarm is activated. Similarly, during a time when the upstream pinching cam closes the upstream follower against the tubing, the output of the photodetector decreases, indicating deceased total internal reflection caused by a widening of the contact line due to pressure in the tubing, a downstream occlusion alarm is activated.

This occlusion sensing system is simple, rugged, reliable and inexpensive. It permits a single sensor to measure both upstream and downstream occlusions, without requiring precise alignment of the administration set within the pump.

BRIEF DESCRIPTION OF THE DRAWINGS

The preferred embodiment of the present invention is illustrated in and by the following drawings in which like reference numerals indicate like parts and in which.

DETAILED DESCRIPTION OF A PREFERRED EMBODIMENT

Figure 1:
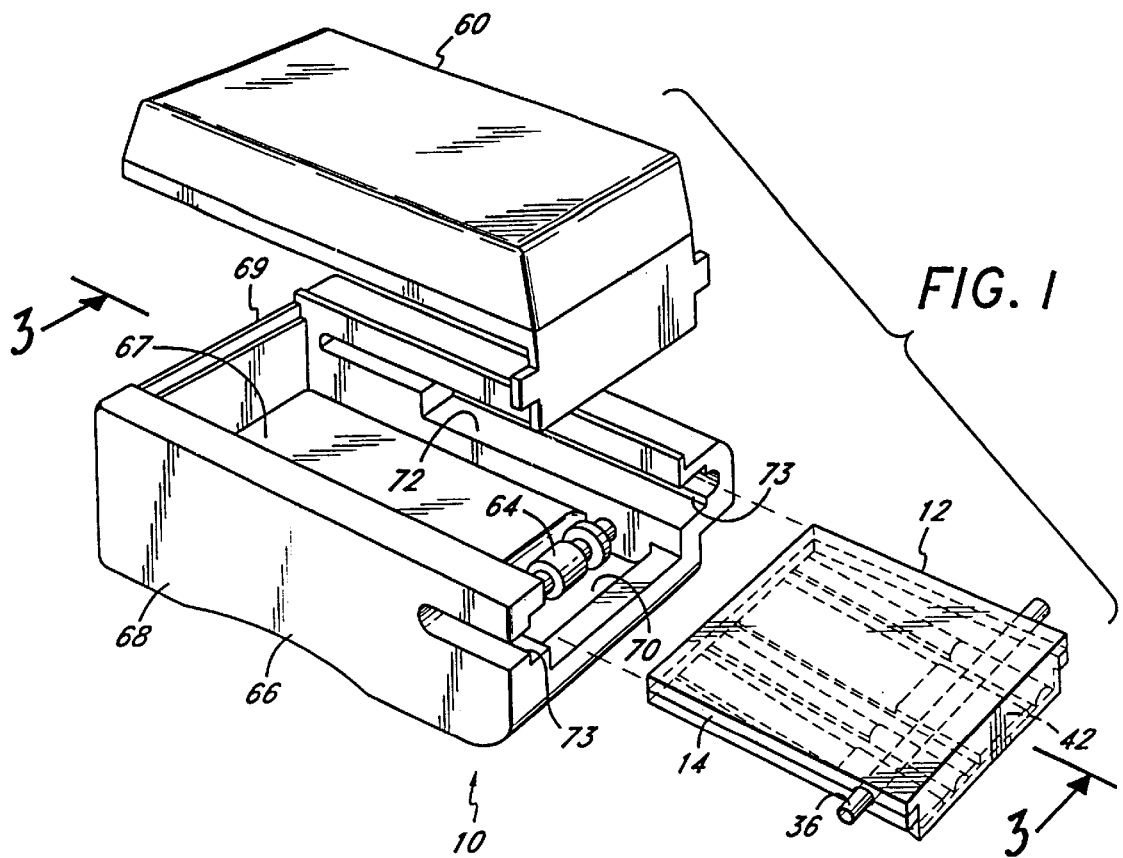
FIG. 1 is a perspective, exploded view illustrating an infusion device having a disposable administration set in accordance with the present invention.
Figure 2:
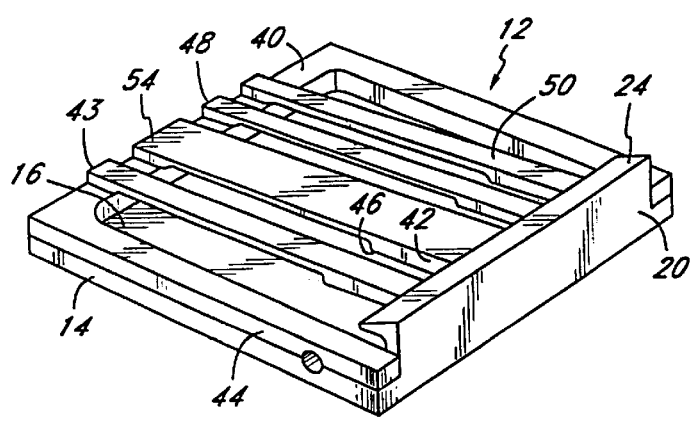
FIG. 2 is a perspective view illustrating a disposable administration set for use with the infusion device of FIG. 1.

FIG. 1 illustrates the infusion device 10 of the present invention for administering intravenous fluid at a consistent and uniform rate. The infusion device 10 is designed to be small, lightweight and ambulatory. The infusion device 10 includes a disposable administration set 12 having a plurality of cam followers 42 which are displaced in a predetermined sequence when depressed by a pumping mechanism 64 to squeeze a delivery tube 36 for dispensing fluid. In FIGS. 1 and 2, a simplified administration set 12, without provision for the occlusion sensor of the present invention, is shown, and will be used to explain the operation of the device 10 by way of background.

The pumping mechanism 64 is driven by a commercially available motor 11 (not shown). The disposable administration set 12 loads easily into the housing structure 66 adjacent the pumping mechanism 64. Oriented directly above the housing structure 66 is an optional fluid reservoir 60 which provides a continuous flow of fluid to the inlet of the delivery tube 36 for dispensing and infusing fluid into a patient's body. Alternatively, the fluid delivery tube 36 may connect to an external reservoir (not shown), or the reservoir 60 may be located at other positions on the assembly.

Figure 3:
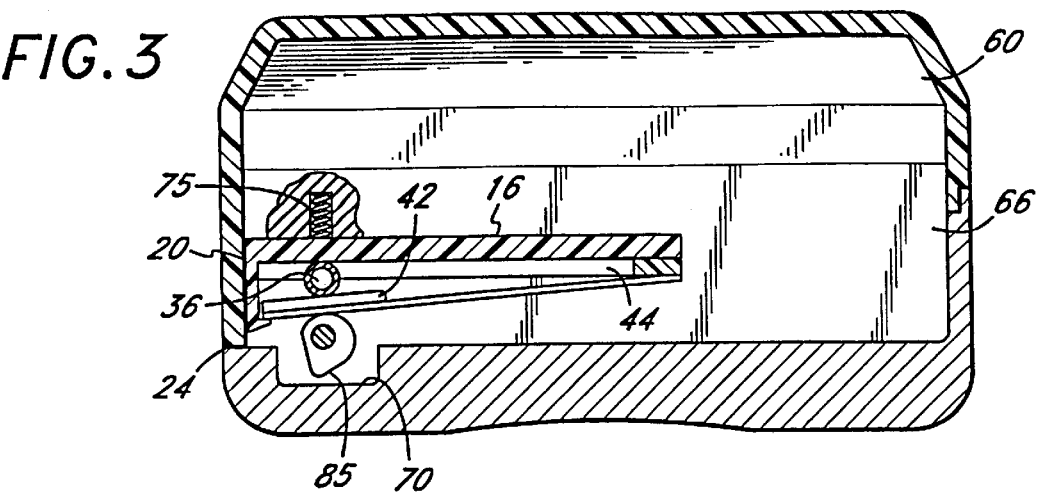
FIG. 3 is a cross section view taken along the line 3—3 of FIG. 1.

The housing structure 66 comprises a rectangular chamber 67 surrounded by side walls 68 and a rear wall 69. The floor of the rectangular chamber 67 drops into a recess 70 towards the front end. The pumping mechanism 64 is located within the recess 70. Extending throughout the length and parallel to the base of each of the side walls 68 is a narrow channel 72 having a lower shoulder 73. The disposable administration set 12 slides within the channel 72. As best seen in FIG. 3, each of the channels 72 includes a spring-biased ball assembly 75. The disposable administration set 12, while being manually inserted into the channels 72, depresses the spring assemblies 75. After insertion of the set 12, the spring assemblies on either side bias the disposable administration set 12 against the shoulders 73 of the channels 72, holding the disposable administration set 12 accurately in position. In operation, the disposable administration set 12 is manually loaded into the infusion device 10 in a simple sliding operation. As the administration set 12 slides into the infusion device, the cam followers 42 are gradually pushed against the delivery tube 36 by the pumping mechanism 64.

Figure 6:
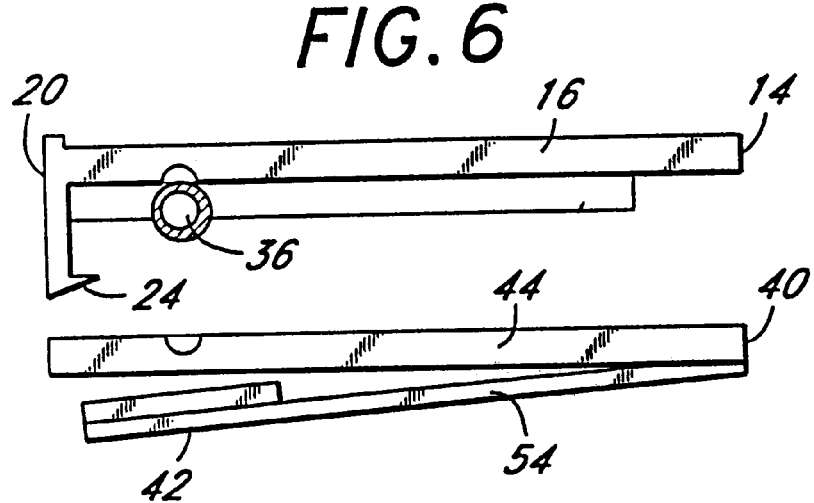
FIG. 6 is a side elevation exploded view illustrating the cam follower and spacer assembly and the plate assembly.

FIGS. 2 and 6 illustrate the simplified disposable administration set 12 without the occlusion sensing of the present invention. The disposable administration set 12 is formed from rigid transparent plastic or the like, and includes a tubing retainer plate assembly 14 which may advantageously be injection molded as a single piece.

The tubing retainer plate assembly 14 includes a tubing retainer plate 16 having a flat tube-contacting surface and a cam follower retainer 20 projecting normal to this surface at one end. The cam follower retainer 20 terminates in a an overhanging latch 24 projecting substantially parallel to the retainer plate 16. The latch 24 serves as a locking mechanism for holding the cam followers 42 in position, adjacent the tube 36 prior to insertion of the administration set 12 into the housing 66. During insertion of the administration set 12 into the channels 72, some of the cam followers 42 are depressed by the pumping mechanism 64. Between pumping cycles of the various cams, the followers return to a standby position against the latch 24.

Figure 5:
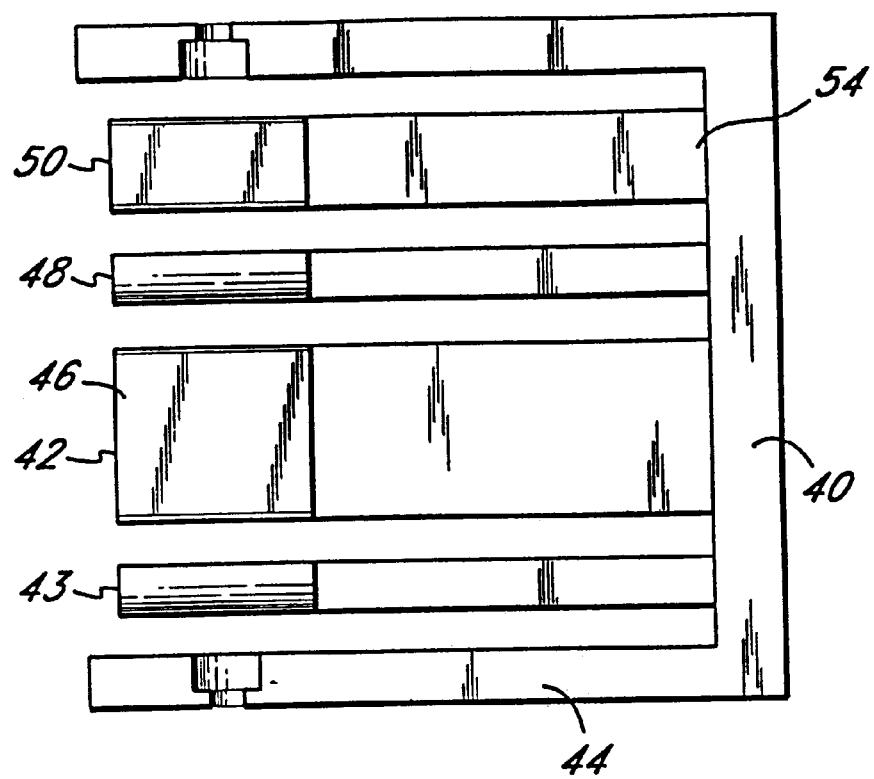
FIG. 5 is a plan view illustrating a can follower and spacer assembly of the present invention.

As best seen in FIGS. 2, 5 and 6 the disposable administration set 12 further includes a cam follower and spacer assembly 40. In the preferred embodiment of the present invention the cam follower and spacer assembly 40 may also be injection molded as a single piece independent of the tubing retainer plate 16. Alternatively, the cam follower and spacer assembly 40 may be molded as one piece with the tubing retainer plate assembly 14 provided that a hinge is molded to connect the cam follower and spacer assembly 40 to the tubing retainer plate assembly 14. The cam follower and spacer assembly 40 includes two gap correction spacers 44 in the form of elongated extending finger-like projections which flank the tubing retainer plate 16 on either side (as best seen in FIG. 2). Since the cam followers 42 are instrumental in controlling the amount of fluid dispensed, the thickness of the cam followers 42 is a critical dimension which directly effects the volume of the delivery tube 36. The accurate pinching of the delivery tube 36 is necessary to allow a desired flow of fluid through the available passage. However, due to typical molding process variations such accuracy may not be possible. The gap correction spacers 44 advantageously counteract these thickness variations. During the molding process, the thickness of both the cam followers 42 and the gap spacers 44 will vary by the same amount, because they are formed in the same mold cavity. Thus, any molding variations, such as those due to mold temperature or pressure, will affect both of these parts identically.

Referring to FIG. 3, it will be seen that, after insertion of the administration set 12 into the housing 66, the dispensing tube 36 is positioned immediately below the siring-biased retainer 75. The spring-biased retainer 75 holds the administration set accurately in place against the shoulders 73 (as best seen in FIG. 1) as described earlier. The cam followers 42 are pushed against the tube 36 by a plurality of cams 85, one of which is shown in FIG. 3. Pumping is accomplished, as will be described below, by squeezing the tube 36.

The gap correction spacer 44 rests between the plate 16 and the shoulder 73 (as best seen in FIG. 1). Thus, if the spacer 44 is thicker than normal, the plate 16 will be positioned further from the cam 85 than normal. However, in this case, as explained above, the cam followers 42 will also be thicker than normal offsetting the effect of the thicker spacer 44. It is advantageous, in accomplishing this self correction, that the thickness of the spacer 44 be the same as that of the active part of the follower 42, so that they will vary identically in thickness.

The plurality of cam followers 42, as best seen in FIG. 5, includes an inlet pincher cam follower 43, a primary, upstream, inlet pumping cam follower 46, an outlet pincher cam follower 48, and a secondary, downstream, outlet pumping cam follower 50. Each of the cam followers 42 are attached to the cam follower and spacer assembly 40 by flexible cam follower arms 54. Each of the cam followers 42 are displaced toward the delivery tube 36 in a predetermined sequence. The inlet pincher cam follower 43 and the outlet pincher cam follower 48 deform the fluid delivery tube 36 to close it off, and thus act as valves. The primary pumping cam follower 46 and the secondary pumping cam follower 50 pump the fluid through the delivery tube 36. The primary pumping cam follower 46 which contacts he upstream segment of the delivery tube 36 is approximately twice the width of the secondary pumping cam follower 50, and it thus squeezes twice the length of tubing. This facilitates displacement of enough fluid during a pumping stroke for delivering fluid external to the pump and at the same time delivering fluid to the downstream segment of the fluid delivery tube 36, beneath the follower 50, to allow it to fill. Thus, as the follower 46 is being advanced toward the tube 36, the follower 50 is being withdrawn. The fluid displaced by the follower 46 fills the tube 36 as it is released by the follower 50, and also supplies enough fluid to continue the outflow from the pump.

Figure 4:
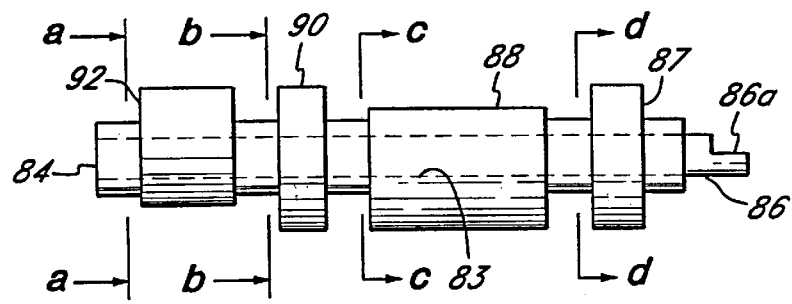
FIG. 4 is a plan view illustrating the single-piece cam of the invention.

Referring now to FIG. 4, the pumping mechanism 64 which provides a continuous and uniform flow will be described. The pumping mechanism 64 comprises a cam assembly 84 and an axle shaft 86. In the preferred embodiment, the cam assembly 84 is preferably formed and machined from a single piece of metal. Alternatively, the cam assembly 84 may be cast, and later machined. As shown, the assembly 84 includes a central aperture 83 to accommodate an axle shaft 86. The shaft 86 may include a flat 86a to couple the shaft 86 to a motor. The axle shaft 86 rotates within bearings which are in turn mounted in two apertures formed within the walls 68 as best seen in FIG. 1. The axle shaft 86 driven by the motor provides rotation to the cam assembly 84. The cam followers 42 are displaced in a predetermined sequence, as described below, thereby squeezing the delivery tube 36 and dispensing a specified volume of fluid.

The cam assembly 84 is specifically designed such that each incremental angle of revolution displaces the same amount of fluid. The cam assembly 84 includes the plurality of spaced cams 85. The plurality of spaced cams 85 include an inlet pincher cam 87, a primary, upstream, inlet pumping cam 88, an outlet pincher cam 90 and a secondary, downstream, outlet pumping cam 92. The inlet pincher cam 87 and the primary pumping cam 88 are operably associated with the inlet pincher cam follower 43 and the primary pumping cam follower 46, respectively. Similarly, the outlet pincher cam 90 and the secondary pumping cam 92 are likewise operably associated with the outlet pincher cam follower 48 and the secondary pumping cam follower 50.

Figure 4A:
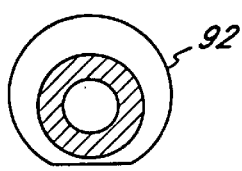
FIG. 4a is a cross section view taken along the line a—a of FIG. 4 illustrating the contour of the outlet or secondary or downstream pumping cam of the present invention.
Figure 4B:
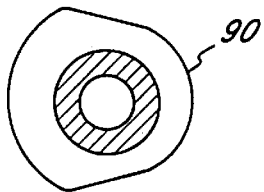
FIG. 4b is a cross section view taken along the line b—b of FIG. 4 illustrating the contour of the outlet pinching cam of the present invention.
Figure 4C:
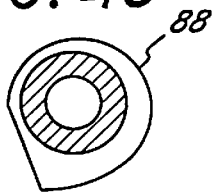
FIG. 4c is a cross section view taken along the line c—c of FIG. 4 illustrating the contour of the inlet or primary or upstream pumping cam of the present invention.
Figure 4D:
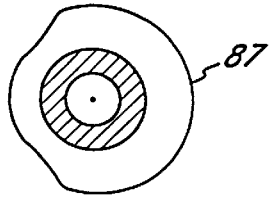
FIG. 4d is a cross section view taken along the line d—d of the present invention illustrating the contour of the inlet pinching cam of the present invention.

Referring to FIGS. 4b and 4d the inlet pincher cam 87 and the outlet pincher cam 90 will be described. The inlet pincher cam 87 and outlet pincher cam 90 operate as valves for the pumping action. The surfaces of the pincher cams 87, 90 are contoured such that between specified rotational positions either the upstream or the downstream segment of the tube 36 is pinched off to obstruct fluid flow.

Referring to FIGS. 4a and 4c, the primary pumping cam 88 and the secondary pumping cam 92 include active pumping surfaces which are uniquely contoured so that the fluid delivery tube 36 is squeezed in such a manner that a constant speed of rotation of the axle shaft 86 results in a uniform or constant displacement of fluid volume from the appropriate segment of the fluid delivery tube 36. To accomplish this result, the primary pumping cam 88 and the secondary pumping cam 92 surfaces are contoured based upon the following principles and calculations.

The equation defining the volume of a cylindrical tube with 1 representing the length and d the inside diameter is as follows:

$$V_{cyl} = \text{length} \times \text{area}$$
$$= l \times \pi d \times \frac{d}{4}$$

The equation defining the volume of an elliptical tube with g representing the inside edge diameter or minor gap and L representing the portion of the cam in contact with the cam follower is as follows:

$$V_{eli} = \text{length} \times \text{area}$$

$$= l \times \pi \times g \times \frac{g}{4} + L \times g$$

Since the circumference of the tube 36 remains relatively constant when the tubing is deformed from a cylindrical shape into an elliptical shape by the cam followers 42, the cylindrical circumference equals the elliptical circumference.

$$C_{eli} = C_{cyl}$$

Additionally the circumference of a cylinder and an ellipse are defined as $C_{cyl} = \pi d$ and $C_{eli} = 2 \times L + \pi \times g$, respectively.

Thus since the circumference remains constant throughout the deformation process of the delivery tube 36, the two circumferences may be equated as follows:

$$\pi \times d = 2 \times L + \pi \times g$$

Solving for L $$L = (\pi \times d - \pi \times g)/2$$

and substituting for area $$\text{area} = g \times L + \pi \times g \times g/4 = g \times (\pi \times d - \pi \times g)/2 + \pi \times g \times g/4$$

$$\text{area} = (\pi/2) \times g \times d - (\pi/4) \times g \times g$$

considering that g=d as the total area displaced and breaking that total area into 100 equal area increments $$\text{total area} = \pi \times d \times d/4$$

and the $$\text{incremental area change} = \pi \times d \times d/400$$

and then solving for the 100 g values corresponding to each of the 100 incremental area increments $$\text{area } 1 = (\pi/2) \times g \times d - (\pi/4) \times g \times g = \pi \times d \times d/400$$

and solving for g given the constant cylinder d value and letting $$K = \pi \times d \times d/400 \text{ for simplification}$$

and letting $\pi/4 = c$ for simplification $2 \times c \times d \times g - c \times g \times g - k = 0$ and solving for the second incremental area $$2 \times c \times d \times g - c \times g \times g - 2 \times k = 0$$

and calculating the remaining 98 equal area increments.

An incremental part of the cam rotation is selected for filling and the remaining part of the rotation will be for pumping. For example, if 180° is selected for pumping, then each incremental area change will occur in 1.8° increments such that the g for the first incremental area will occur at 1.8 degrees, the g for the second incremental area will occur at 3.6 degrees, etc. Finally, the g for the 100th area will occur at 180 degrees. The cam radiuses at each increment can then be calculated by subtracting the required g value from the displacement between the center of the cam to the face of the plate assembly minus the cam follower thickness minus 2 times the tubing wall thickness plus the gap spacer thickness.

Using this derivation, it is possible to generate the proper cam pumping profile for any combination of tube diameter, cam spacing, tube wall thickness, and cam-degrees of pumping rotation.

The relationship between the cam radius and the tubing gap is algebraically proportional only when the cam radius in constant. As the cam radius changes, the effect of the approximately horizontal surface of the follower, contacting the changing cam surface makes it necessary to take the phase and amplitude into consideration. For example, a rapidly increasing cam surface results in a gap change that leads the actual radius change. Likewise, a rapidly decreasing cam radius results in a gap change that lags the actual radius change. The amount of change in phase is a function of a ratio of the beginning and ending cam radii.

The present invention utilizes approximate predicted phase changes based on calculations, of the ratio of the beginning and ending cam radii, relative to the rotational positions of the cam. This effect is more significant in the case of the rapidly changing pincher cams which are characterized by transitioning phase changes of approximately 35 degrees. Thus, once the cam profiles and approximate rotational positions of each cam are selected, the actual gaps are numerically computed as described. For each degree of rotation, each radius has a vertical component which is computed by multiplying the actual radius length by the cosine of the angle that is formed by that radius relative to a vertical line. The vertical line passes through the center of the axle shaft and is approximately normal to the surface of the cam follower. The vertical component of each radius thus changes as the cam rotates about its axis. Since the follower is formed to contact the cam surface in an approximately downward direction, for a particular degree of rotation of the cam, the cam follower will contact the cam surface at the radius which has the greatest positive vertical component. The actual radius of contact at each degree of rotation is determined by numerically computing the radius with the greatest vertical component at each degree of rotation.

Figure 7:
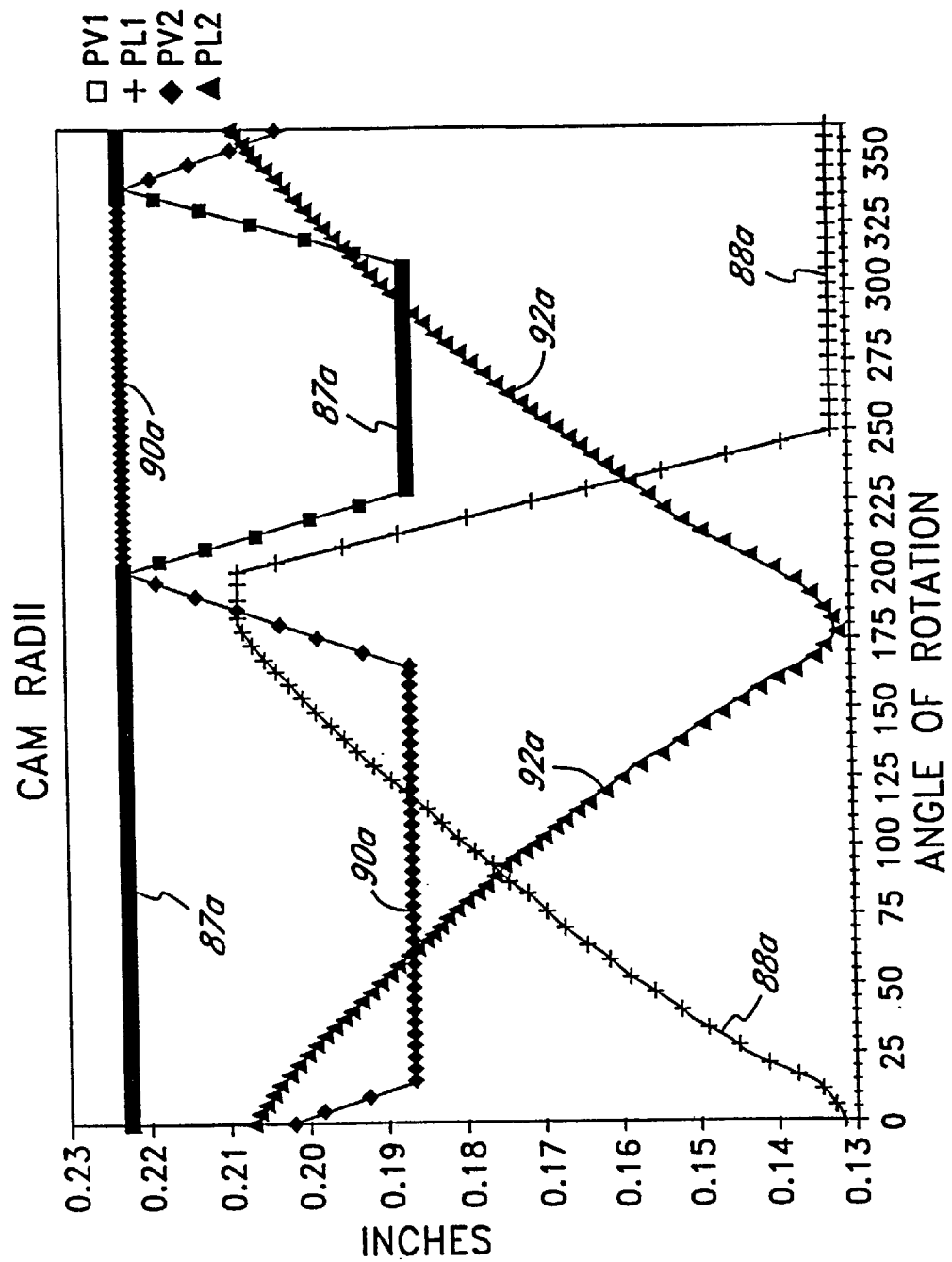
FIG. 7 is a graphical representation of the cam radii versus the angle of cam rotation of the present invention.

Referring to FIGS. 4 and 7 the operation of the cams 85 relative to the gap of the delivery tube 36 will be described. The cam assembly 84, as seen in FIG. 4, rotates about the axle shaft 86 and acts through the cam followers upon the delivery tube 36 positioned directly beneath the cam assembly 84. As best seen in FIG. 7, between the rotational positions 0 degrees and 200 degrees the inlet pincher cam 87, indicated by a curve trace 87a, forces the inlet cam follower 43 to pinch off the upstream segment of the tube 36 to prevent fluid flow back into the reservoir 60. While the upstream segment of the tube 36 is pinched off, the primary pumping cam 88 progresses through a gradual pumping stroke lasting from 0 degrees to approximately 175 degrees, indicated by the curve 88a. This displaces the inlet pumping cam follower 46 against the tube 36 to squeeze enough fluid to the downstream segment as well as external to the pump to continue to provide a uniform and consistent flow while the tube 36 beneath the secondary pumping cam 92 is filling. This filling is caused by a reduction in the diameter of the cam 92 through this rotational segment, as shown by curve 92a.

Once the downstream segment of the tube has been filled with fluid (at approximately the 180 degree rotation point), the outlet pincher cam 90 closes and remains closed between the rotational angles 200 degrees to 340 degrees, indicated by the curve 90*a*. This forces the outlet cam follower 48 to pinch off the downstream segment of the delivery tube 36. When the cam 90 pinches the tube 36 at approximately the 180 degree rotational position, the cam 87 rotates to a reduced diameter region which extends between approximately 220 degrees and 340 degrees. This opens the tube 36 beneath the cam 87, as shown by curve 87*a*, to allow fluid to flow from the reservoir 60 to the portion of the tube 36 which underlies the cam 88, so that this tube portion may fill. This allows the upstream segment to fill in response to a gradual reduction in the radius of the cam 88, as shown by the curve 88*a* between 220 degrees and 340 degrees. During this segment, the secondary pumping cam 92, indicated by the curve 92*a*, depresses the secondary cam follower 50 against the tube 36 dispensing fluid external to the pump.

Figure 8:
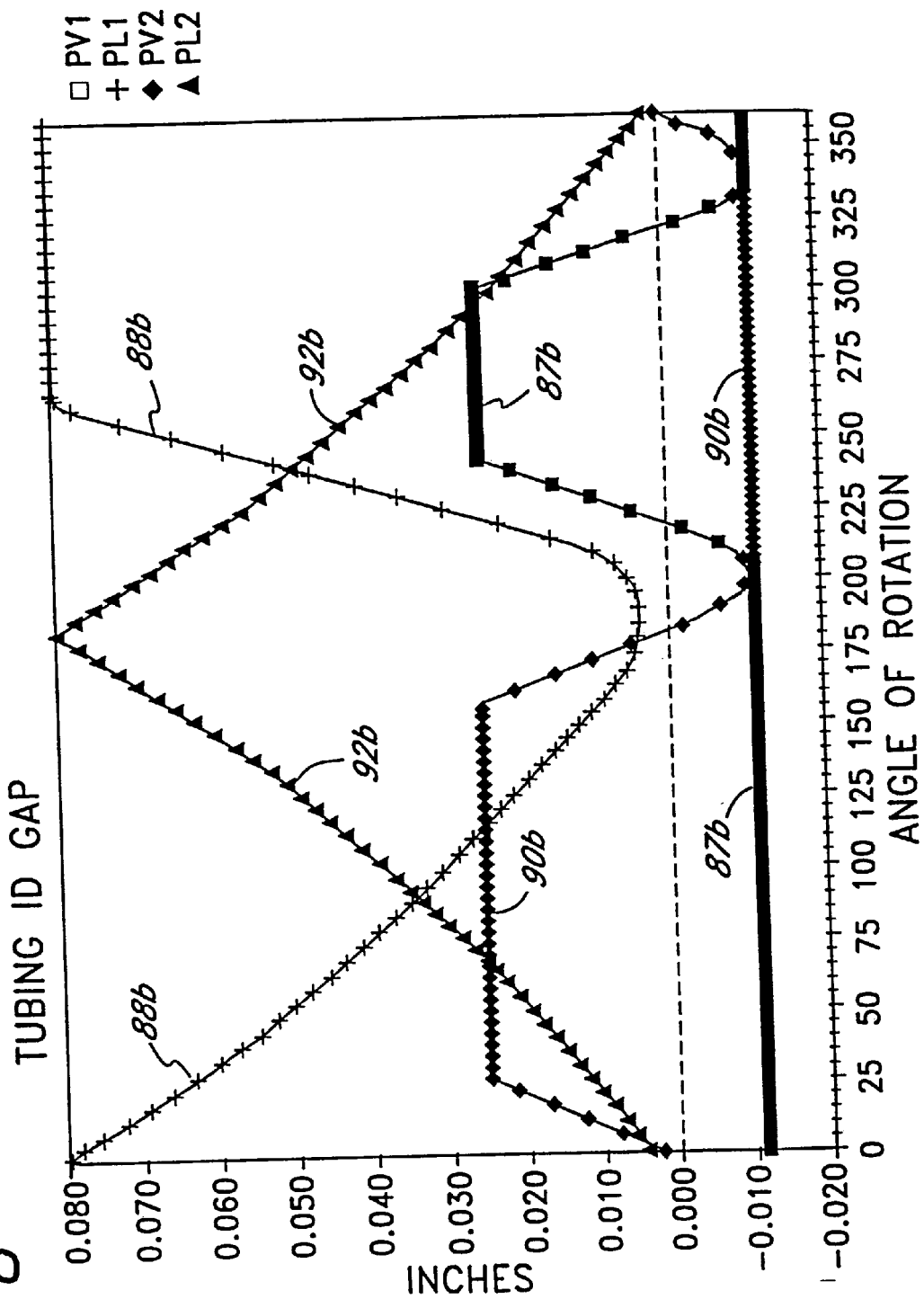
FIG. 8 is a graphical representation of the tubing ID gap versus the angle of cam rotation of the present invention.

Referring to FIG. 8, the affect of the cams 85 on the tubing gap during their rotational movement is shown. The curves of FIG. 8 are thus somewhat inversely proportional to the curves of FIG. 7, since an increase in cam radii causes a decrease in the corresponding tube 36 gap, taking into account the fact that the gap change leads the actual radius change. The upstream segment of the tube 36, indicated by the curve 87*b* is completely pinched off between the rotational positions 340 degrees and 200 degrees. The primary pumping cam 88, as described above, reduces the gap beneath it to expel fluid until it reaches a rotational angle position of 175 degrees, as indicated by the curve 88*b*. The gap of the tube 36 beneath the cam 92 is gradually increased during this segment between 0 degrees and 180 degrees, so that the tube 36 beneath the secondary pumping cam 92 will slowly fill with fluid.

Once the downstream segment of the tube 36 has been filled, the outlet pincher cam 90 causes the downstream segment to be pinched off as indicated by the curve 90*b* so that the secondary pumping cam 92 can deliver fluid external to the pump. The tubing gap beneath the cam 92 varies as indicated by the curve 92*b* during the pumping stroke (175 degrees to 360 degrees) of the secondary pumping cam 92.

Figure 9:
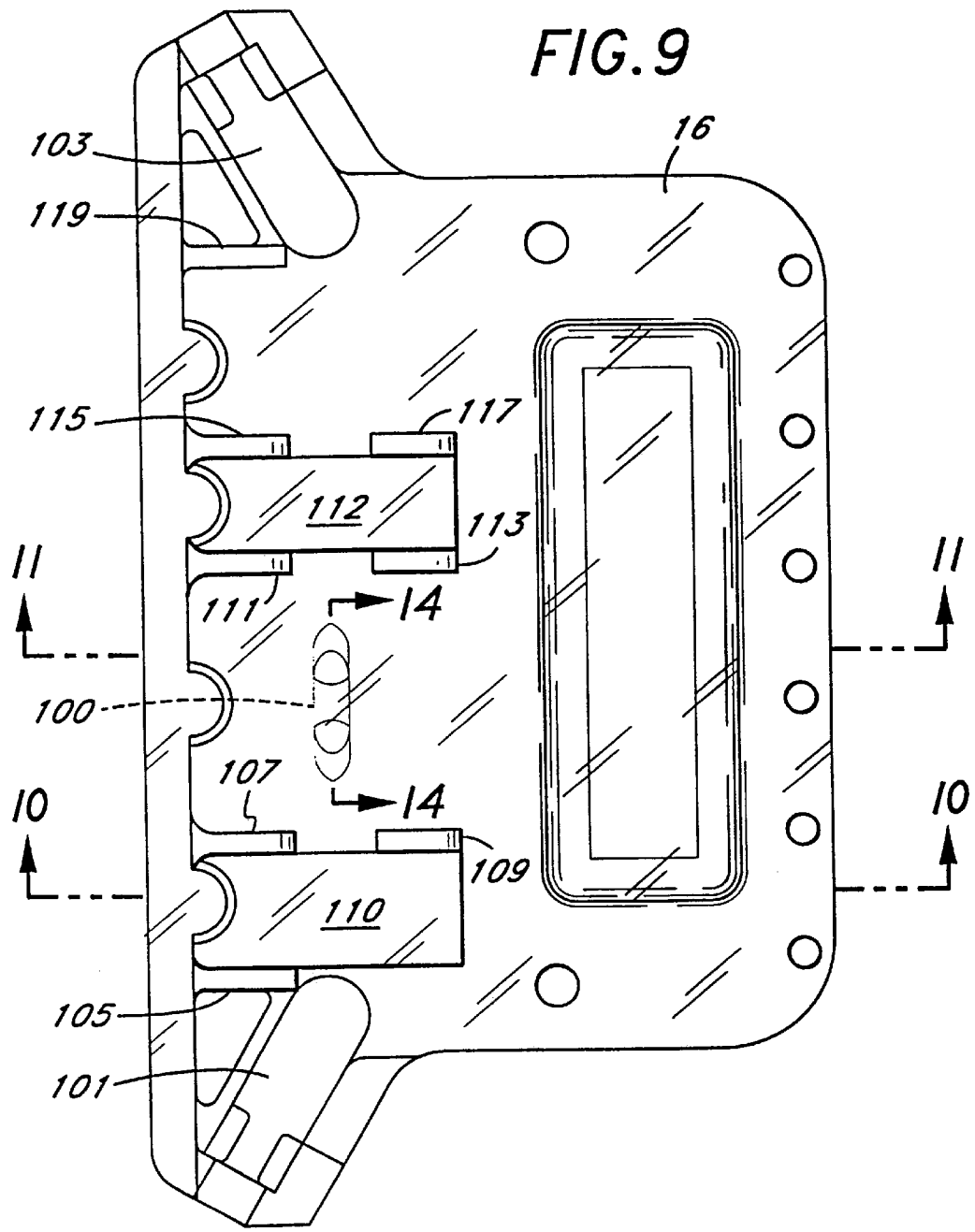
FIG. 9 is a plan view of an the tubing retainer plate of the administration set of this invention, showing the optical path elements for the occlusion detection system.

Referring now to FIG. 9, the construction and operation of the occlusion sensing system of this invention will be described. FIG. 9 shows the tube-retaining surface, that is, the lower surface as viewed in FIG. 1, and the upper surface as viewed in FIG. 2, of the tubing retainer plate 16 of the disposable administration set 12. This plate is transparent, and thus an occlusion sensing recess 100 can be seen through the plate 16 in the view of FIG. 9, though this recess is located on the underside of the plate 16 in this view.

Figure 10:
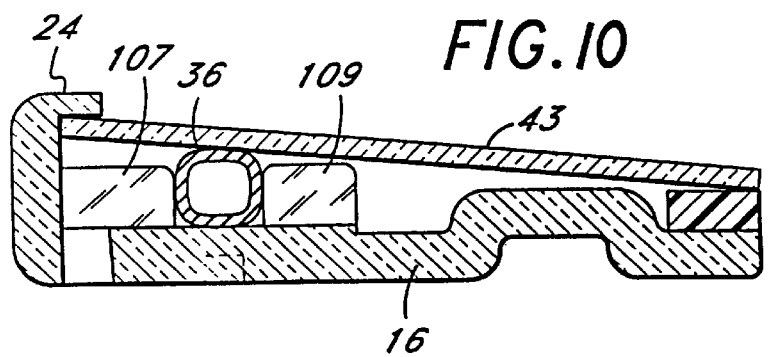
FIG. 10 is a sectional view of the tubing retainer plate of FIG. 9, taken along line 10—10 of FIG. 9, along with a broken away portion of the infusion device body, showing the positional relationship of the retainer plate when the administration set is installed in the infusion device.

An inlet tubing aperture 101 guides the inlet tubing from the medication source to the upper surface of the tubing retainer plate 16. In a similar fashion, an outlet tubing aperture 103 guides this same tube 36 from the surface of the tubing retainer plate 16 to the patient. Between these two apertures 101, 103, the tubing is guided, under slight tension, across the upper surface of the plate 16 between a series of stanchions. A first stanchion 105 and a last stanchion 119 form fulcrums around which the tubing is bent as it enters and exits the plate 16, so that the tubing can extend straight across the face of the plate 16 therebetween. Between the first stanchion 105 and a pair of opposed stanchions 107, 109, the surface of the plate 16 is raised by approximately 0.020 inches in a small region 110. This region 110 is also shown in FIG. 10, and is opposite the inlet pinching cam follower 43, and the raised surface 110 assists in assuring that the tubing will be completely pinched off by the cam follower 43.

Similarly, between a pair of stanchions 111, 113 and another pair 115, 117, the surface of the plate 16 in a region 112 is raised by 0.020 inches at a location opposite the pinching cam follower 48 for the same reason.

When the tubing is in place on the plate 16, it is held against the regions 110 and 112 by the opposed pinching cam followers 43, 48, which are in turn held down by the latch 24 (FIG. 2).

Between the stanchions 107, 109 and the stanchions 111, 113, because the tubing is under slight tension, the tubing is actually suspended above the surface of the plate 16, unless held against that surface by the follower 46.

Figure 11:
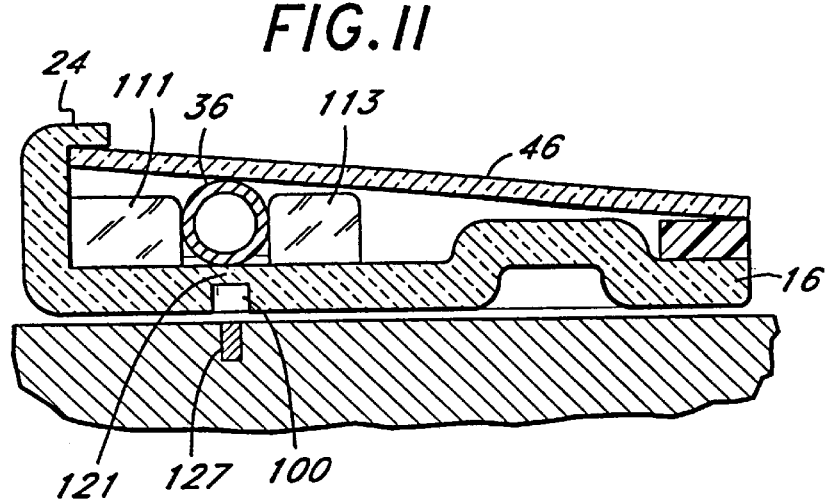
FIG. 11 is a sectional view of the tubing retainer plate of FIG. 9, taken along line 11—11 of FIG. 9, showing the positional relationship of the tubing and the retainer plate when the administration set is installed in the infusion device, and neither the inlet nor the outlet tubing is occluded.

At a location midway between the stanchions 107, 109 and 111, 113, on the underside of the plate, as viewed in FIG. 9, and as shown in cross section in FIG. 11, there is a specially formed recess 100 for the occlusion sensing system of this invention. It should be noted that this position of the recess 100 is significant, as it underlies a portion of the tube 36 which is beneath the follower 46, and is between the pinching followers 43 and 48. Because of this location, the tubing located above the recess 100 is in direct fluid communication with the upstream (supply) tubing when the pinching follower 43 is open, and the pinching follower 48 is closed. This occurs, as can be seen from FIGS. 7 and 8, following the 200 degree position and up until the following 335 degree position the cam assembly. (Note that curves 87*a* and 87*b* relate to the movement of the follower 43, while curves 90*a* and 90*b* relate to the movement of the follower 48.) In addition, at this location, the tubing located above the recess 100 is in direct fluid communication with the downstream (outlet to patient) tubing when the pinching follower 43 is closed, and the pinching follower 48 is open. This occurs, as can be seen from FIGS. 7 and 8, following the 335 degree position, and up until the following 200 degree position of the cam assembly. As a consequence, it is possible with a single sensing system to detect occlusions in both the upstream and downstream connections to the infusion device.

FIGS. 7 and 8 demonstrate that the pumping follower 46 is in a fully raised position following the 250 degree position, and up until the 360 degree position (Illustrated by curves 88*a* and 88*b*). Thus, following the 250 degree position and up until the 335 degree position, the follower 46 is at its fit position away from the plate 16, and the tubing is at its maximum diameter and in communication with the upstream or supply portion of the tubing. Similarly, following the 335 degree position, and until the 360 degree position, the follower 46 is at its furthest position away from the plate 16, and the tubing is at its maximum diameter and in communication with the downstream or patient portion of the tubing.

Figure 12:
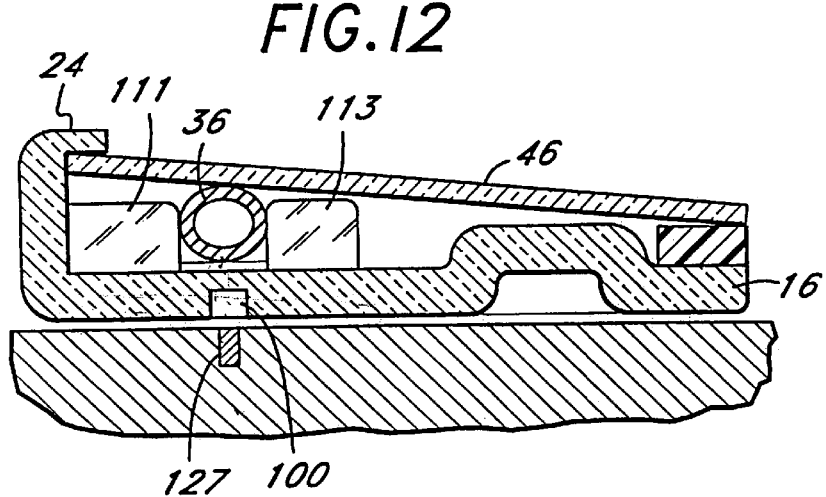
FIG. 12 is a sectional view of the tubing retainer plate of FIG. 9, taken along line 11—11 of FIG. 9, identical to FIG. 11, but showing the positional relationship of the tubing and the retainer plate when the administration set is installed in the infusion device and the inlet tubing is occluded.
Figure 13:
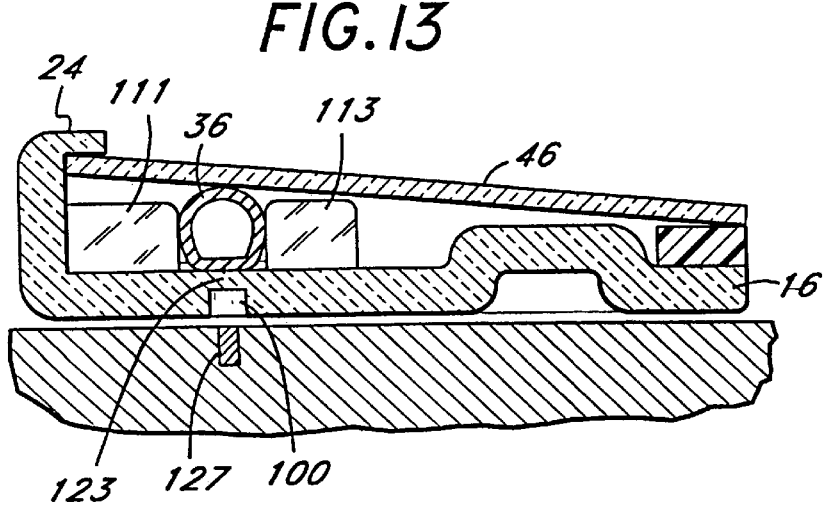
FIG. 13 is a sectional view of the tubing retainer plate of FIG. 9, taken along line 11—11 of FIG. 9, identical to FIGS. 11 and 12, but showing the positional relationship of the tubing and the retainer plate when the administration set is installed in the infusion device and the outlet tubing is occluded.

Referring now to FIGS. 11, 12 and 13, the condition of the tubing immediately opposite the recess 100 and under various operating conditions will be described. In each of these figures, the follower 46 is shown at its raised position, that is, the position furthest away from the plate, so that the tubing is at its maximum diameter. In FIG. 11, the tubing is in its normal condition, that is, neither expanded from pressure nor contracted from vacuum within the tube 36. In this condition, between the 250 degree position and the 360 degree position, the tubing is held against the surface of the plate 16 by the follower 46 so that a relatively narrow region 121 of the tube 36 is in contact with the plate 16 opposite the recess 100. The follower 46 is held in position by the latch 24, so that the extent of tube 36 contact with the plate 16 is predetermined.

FIG. 12 shows the condition of the tube 36 between the 250 degree position and the 335 degree position, when a vacuum is drawn within the tube 36. The outside diameter of the tube 36 is reduced by the vacuum so that the tube 36 cannot fill the distance between the surface of the plate 16 and the follower 46. Because the tube 36 is under slight tension, and is stretched between the raised regions 110, 112 (FIG. 9), the tube 36 will lift away from the surface of the plate 16 under these conditions, so that there will be no contact between the tube 36 and the plate 16 opposite the recess 100.

FIG. 13 shows the condition of the tube 36 between the 335 degree position and the 360 degree position, when the medication within the tube 36 is under pressure. The outside diameter of the tube 36 is increased by the pressure so that the walls of the tube 36 flatten out against the surface of the plate 16 and the follower 46. This flattening will increase the width of the region 123 of contact between the tube 36 and plate 16 opposite the recess 100.

As will be seen from the following description, the extent of contact between the tube 36 and plate 16 is used to sense occlusions within the tubing.

Figure 14:
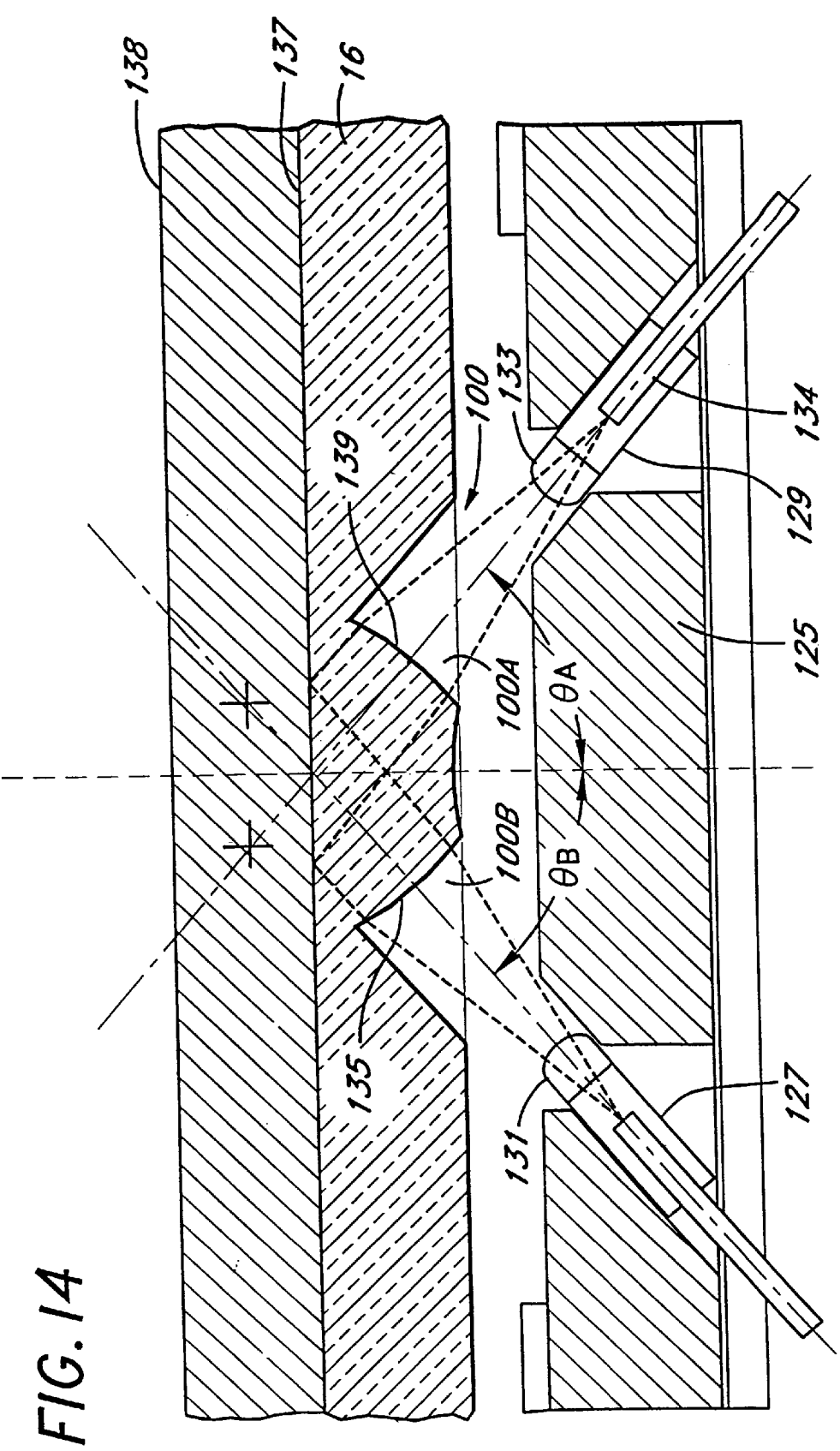
FIG. 14 is a sectional view of the tubing retainer plate of FIG. 9, taken along line 14—14 of FIG. 9, along with a broken away portion of the infusion device body and the adjacent wall of the tubing, showing the positional relationship of the retainer plate and the occlusion sensors when the administration set is installed in the infusion device.

Referring now to FIG. 14, a greatly enlarged cross sectional view of the portion of FIG. 11 in the region of the recess 100 will be described. The recess 100 is actually a pair of recesses 100a and 100b which are formed to direct light toward the interface of the tubing and the surface of the plate 16. If the angle of incidence of the light with this interface, and the respective refractive indexes, and properly selected, total internal reflection of the light will occur at the interface when the tubing is separated from the plate 16, but will not occur at the interface when the tubing is pressed against the plate 16. The existence or lack of total internal reflection is used to determine the condition of the tubing, and thus the existence of occlusions.

More specifically, within the wall 125 of the reservoir (FIG. 1), a light emitter 127 and a light detector 129 are mounted at respective angles of $(theta)A$ and $(theta)B$, with regard to a line normal to the surface of the wall 125. The wall 125 is parallel to, and slightly spaced from the plate 16 when the administration set 12 is installed in the infusion device 10. The light emitter 127 is typically a LED including a lens 131 which creates a light beam which diverges at approximately 10 (degrees). Similarly, the light detector 129 typically includes a focusing lens 133 suitable for focusing a 10 (degree) converging light beam onto a photodetector 134.

The recess 100b is wedge-shaped and includes a surface 135 formed as a convex lens which is coaxial with the light emitter 127. This lens 135 collimates the light from the emitter 127, and directs the light toward the surface 137 of the plate 16. The surface 137 is adjacent the wall 138 of the tubing. Light which is reflected from the surface 137 is focused by a similar convex lens 139 formed in wedge-shaped recess 100a. This lens 139 is co-axial with the light detector 129, and focuses the reflected light through the lens 133 to the photodetector 134. If the illumination output from the LED 127 is constant, changes in the light level detected by the photodetector indicate the amount of light reflection at the surface 137.

Figure 15:
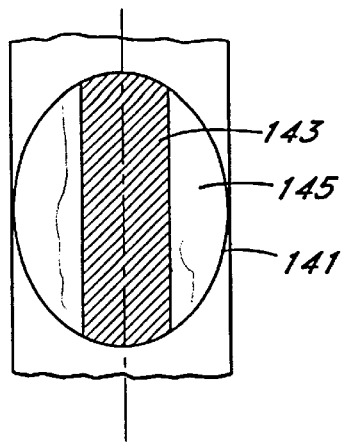
FIG. 15 is a broken-away schematic view showing the view of the tubing retainer plate at the photosensor of the occlusion sensing system.

FIG. 15 illustrates the view of the surface 137 of the plate 16 from the photodetector 129. In this figure, the oval 141 represents the field of view of the photodetector 129. This field of view includes a first region 143 in which the tube 36 is in contact with the surface 137 of the plate 16, and a second region 145 in which the tube 36 is not in contact with the surface 137. As described earlier, the region 143 will widen as the fluid in the tube 36 is pressurized, so that a wider region 123 (FIG. 13) of the tube 36 is pressed against the surface 137. When the tubing is subjected to a vacuum, so that no contact occurs been the plate 16 and the tube 36 (FIG. 12), the region 143 will disappear altogether from the field of view 141. As will be described more fully below, total internal reflection occurs within the region 145, while absorption of the light incident from the LED 127 occurs in the region 143.

Figure 16:
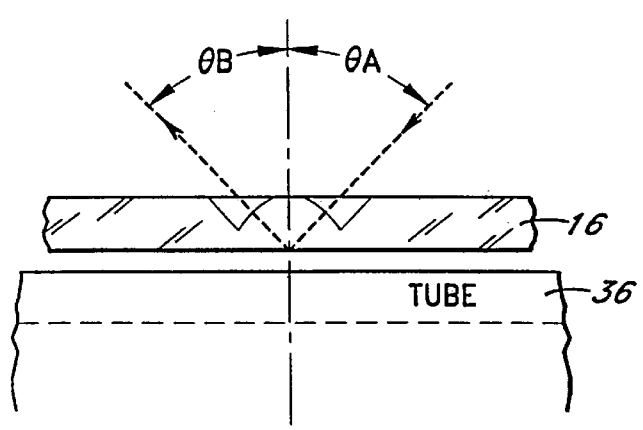
FIG. 16 is a schematic view, similar to the view of FIG. 14, illustrating the light path when there is no occlusion, or when there is a downstream occlusion.

Referring now to FIGS. 16–20, the operation and construction of the occlusion detection system will be described Referring first to FIG. 16, which shows schematically the path of light from the LED 127 when the tube 36 is separated from the plate 16, a condition which will occur if there is an upstream occlusion, such as an empty supply receptacle or a pinched tube between the receptacle and the pump. In this situation, total internal reflection of the incident light should occur at the plate 16/air interface. As will be seen from the following analysis, if the refractive indexes of the plate 16 and tube 36 are known, the angles $\theta_A$ and $\theta_B$ may be derived, so that the LED 127, photodetector 124 and recess 100 may be properly oriented. If the refractive index of the plate 16 is Mp, and the refractive index of air is Ma (1.00), the expression for total internal reflection is $\sin(Theta)a \geq Ma/Mp$. If Mp is 1.55, as is the case for polycarbonate, the plastic used in the preferred embodiment for the plate 16, then $(Theta)a \geq 40.2$ degrees for Total Internal Reflection.

Figure 17:
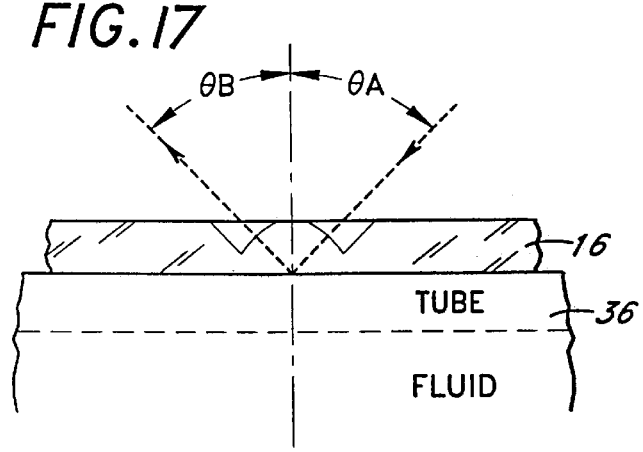
FIG. 17 is a schematic view, identical to FIG. 16, except that it illustrates the light path when there is an upstream occlusion.

Referring now to FIG. 17, the path of light from the LED 127 is shown when the tube 36 is pressed against the plate 125, a condition which will occur at the center of the tube when there is no occlusion, and across a wider region when there is a downstream occlusion which increases the fluid pressure in the tube 36. In this case, absorption of the light should occur at the plate 125/tube 36 interface. If the refractive index of the tube 36, Mf, is 1.40, which is the case for clear PVC, the plastic used in the preferred embodiment for the tube 36, total internal reflection will occur if $\sin(Theta)a \geq Mf/Mp$, i.e, if $(Theta)a$ is greater than 64 degrees. Thus, to assure light absorption under these conditions, $(Theta)a$ must be less than 64 degrees.

From these calculations, it is clear that a range of $(Theta)a$ angles exists (40–64 degrees for the preferred embodiment) which will provide total internal reflection of the light beam when the tube 36 is separated from the plate 125, and absorption of the light beam when the tube 36 is pressed against the plate 125.

Figure 18:
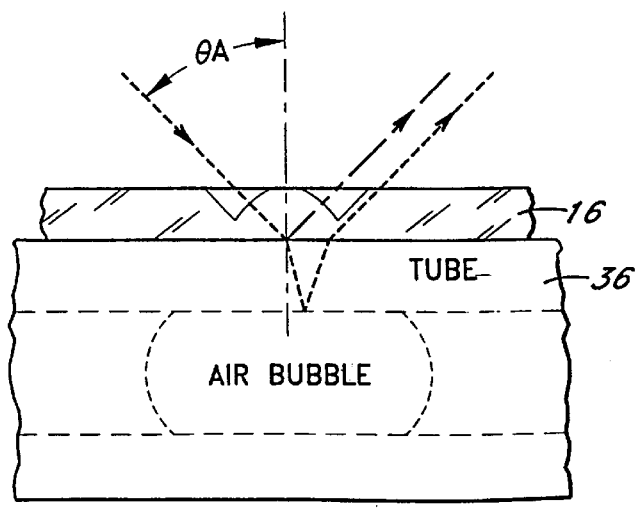
FIG. 18 is a schematic view, identical to FIG. 16, except that it illustrates the light path when there is a bubble in the fluid in the tubing.

Referring now to FIG. 18, the condition in which the tube 36 is pressed against the plate 125, but in which an air bubble, rather than fluid, is in the tube 36, will be described. Assuming light absorption occurs at the interface of the plate 125 and the tube 36, as explained above for the situation where the tube 36 is against the plate 125, total internal reflection can still occur at the tube 36/bubble interface. Due to the passage of the light twice through the tubing wall, and to the fact that the light is reflected off a cylindrical rather than a flat interface, an offset occurs between the direct optical path (shown in dashed lines) and the light path from the tube 36/bubble interface. Thus, light will be reflected back to the photodetector 129, but this offset in the light path will misaligned the light from the photodetector 129, so that more light will be detected than without the air bubble being present, but less light that if the tube 36 is separated from the plate 125.

Figure 19:
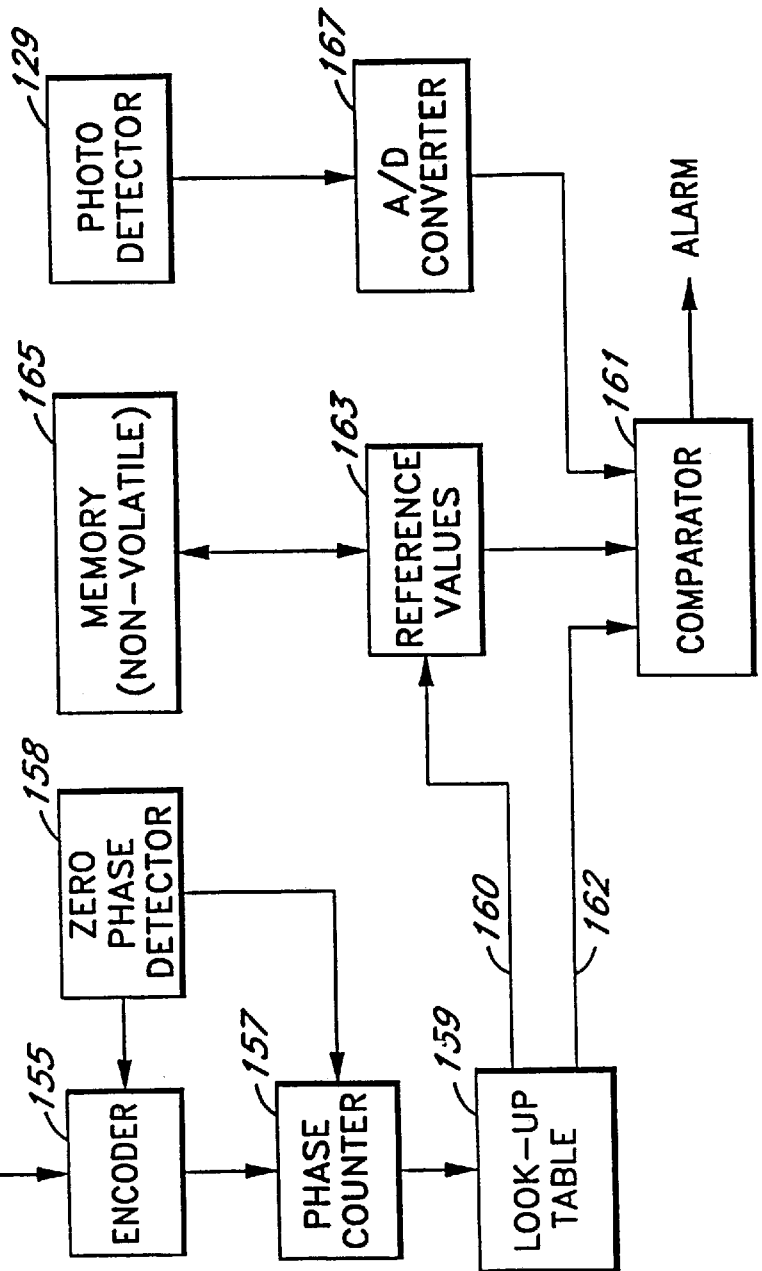
FIG. 19 is a schematic view, identical to FIG. 16, except that it illustrates the light path when there is a downstream occlusion and a fluid leak in the system.

From the above description of FIGS. 16, 17 and 18, it can be seen that the occlusion sensing system of this invention provides a mechanism for detecting a vacuum or high pressure in the tube 36, and for detecting the presence of a bubble in the tube 36. In order to utilize this sensing mechanism to measure both upstream and downstream occlusions, as well as air bubbles in the medication stream, the electronic synchronizing system shown in FIG. 19 is used. A motor 151 rotates the cam of the pump mechanism 153. An encoder 155 is attached to the shaft of the motor 151 to generate a pulse during each incremental revolution of the motor 151. The output of the encoder 155 is accumulated in a phase counter 157 which converts the encoder output into an output corresponding to degrees of rotation of the motor 151. A zero phase detector 158 is used to reset the output of the encoder 155 and phase counter 157 each time the motor rotates to a zero position, such as the zero angle positions of FIGS. 8 and 9. Thus, the output of the phase counter 157, in the preferred embodiment, is a signal, defining motor and cam position, calibrated in terms of degrees of rotation referenced to a zero position as shown in these figures.

A look-up table 159 is connected to the output of the phase counter 157, and provides a first output 160 to a comparator 161 indicative of whether the cam position is appropriate to measure occlusions. As described in detail earlier, following the 250 degree cam position and up until the 335 degree position, the tubing is at its maximum diameter and in communication with the upstream or supply portion of the tubing, permitting upstream occlusion sensing. Similarly, following the 335 degree position, and until the 360 degree position, the tubing is at its maximum diameter and in communication with the downstream or patient portion of the tubing, permitting downstream occlusion sensing. Thus, at a preselected angular position of the cam, such as the 300 degree position, an enable signal is sent from the comparator 161. At the same time, a second output 162 from the look up table 159 indicates that an upstream occlusion is to be measured. In response to the second output 160, a reference value selector 163 selects from a memory 165 the highest appropriate photodetector output level from the photodetector 129 in the absence of an upstream occlusion, i.e., when total internal reflection is not occurring throughout the width of the tube 36 and provides this reference value to the comparator 161. If the output from the photodetector 129, converted in an A/D converter 167, is above this highest appropriate output level, the comparator 161 issues an alarm, indicating that an upstream occlusion has occurred.

Similarly, at a preselected angular position of the cam, such as the 345 degree position, an enable signal is sent from the comparator 161. At the same time, a second output from the look up table 159 indicates that a downstream occlusion is to be measured. In response to this output, a reference value selector 163 selects from a memory 165 the lowest appropriate photodetector output level from the photodetector 129 in the absence of a downstream occlusion, i.e., when light absorption is not occurring throughout the majority of the width of the tube 36 and provides this reference value to the comparator 161. If the output from the photodetector 129, converted in an A/D converter 167, is below this lowest appropriate output level, the comparator 161 issues an alarm, indicating that a downstream occlusion has occurred.

In addition, at this same 345 degree position, another output from the reference value selector 163 selects from the memory 165 the highest appropriate photodetector output level from the photodetector 129 in the absence of an air bubble in the tubing and provides it to the comparator 161, i.e., when total internal reflection is not occurring at the inside diameter of the tubing. If the output from the photodetector 129 converted in the A/D convertor 167 is above this highest appropriate level, the comparator 161 issues an alarm, indicating that a bubble exists within the medication.

Although this invention is described in terms of certain preferred embodiments, other embodiments that are apparent to those of ordinary skill in the art are also within the scope of this invention. Accordingly, the scope of the invention is intended to be defined only by the claims which follow.

What is claimed is:

1. A system for detecting deviations in the flow of fluid through a flexible tube, the flexible tube providing fluid communication between a fluid source and a patient, the system comprising:
   a transparent plate in contact with the flexible tube;
   a light source configured to project light onto the transparent plate in the direction of the flexible tube; and
   an optical sensor disposed such that it is directed at the transparent plate and the tube and is configured to measure reflected light; and
   wherein said transparent plate mounts the flexible tube such that when the flexible tube is in a normal flow condition, it is in contact with the transparent plate and when the flexible tube is exposed to an upstream occlusion condition, the tube has decreased contact with the transparent plate.

2. The system of claim 1 further comprising:
   an infusion pump which provides the flow of fluid through the tube.

3. The system of claim 2 wherein the infusion pump has a housing which holds the transparent plate, the light source and the optical sensor.

4. The system of claim 1 wherein the transparent plate mounts the flexible tube such that the flexible tube has a first level of contact with the transparent plate when under a normal condition at which the tube experiences pressure exerted by the flow of fluid through the tube and a second level of contact with the transparent plate when under an expanded state at which the tube experiences increased pressure caused by a downstream blockage of the flow, wherein the second level of contact with the transparent plate when in the expanded state is a greater level of contact with the transparent plate.

5. The system of claim 1 wherein the transparent plate has an index of refraction which differs from the index of refraction of the flexible tube, such that increased contact between the tube and the transparent plate cause a decrease in the amount of light reflected in a critical angle.

6. The system of claim 5 wherein the optical sensor is positioned to measure the amount of light reflected at the critical angle.

7. A system for detecting deviations in the flow of fluid through a flexible tube, the flexible tube providing fluid communication between a fluid source and a patient, the system comprising:
   a transparent plate in contact with the flexible tube;
   a light source configured to project light onto the transparent plate in the direction of the flexible tube;
   an optical sensor disposed such that it is directed at the transparent plate and the tube and is configured to measure reflected light;
   wherein the transparent plate has s first surface and a second surface, the second surface having a first recess which forms a lens configured to direct light emitted form the light source onto the first surface, and a second recess which forms a lens configured to direct light reflected from the first surface into the optical sensor; and
   means for determining whether the measurements received from the optical sensor indicate either an upstream or downstream blockage in the flow through the tube.

8. The system for detecting deviations in the flow of fluid through a flexible tube, the flexible tube providing fluid communication between a fluid source and a patient, the system comprising:

a transparent plate in contact with the flexible tube;

a light source configured to project light onto the transparent plate in the direction of the flexible tube;

an optical sensor disposed such that it is directed at the transparent plate and the tube and is configured to measure reflected light; and means for determining whether the measurements received from the optical sensor indicate either an upstream or downstream blockage in the flow through the tube, wherein the determining means is capable of distinguishing between upstream occlusions and downstream occlusions.

9. The system of claim 1 wherein the determining means is further capable of identifying an air bubble in the flexible tube.

10. The system for detecting deviations in the flow of fluid through a flexible tube, the flexible tube providing fluid communication between a fluid source and a patient, the system comprising:

a transparent plate in contact with the flexible tube and providing a mounting of the flexible tube wherein the flexible tube has a reference state when under the pressure exerted by the desired rate of flow and a contracted state when under a vacuum exerted by an upstream blockage of the flow, wherein the contracted state has decreased contact with the transparent plate;

a light source configured to project light onto the transparent plate in the direction of the flexible tube;

an optical sensor disposed such that it is directed at the transparent plate and the tube and is configured to measure reflected light; and means for determining whether the measurements received from the optical sensor indicate either an upstream or downstream blockage in the flow through the tube.

11. A system for detecting deviations in the flow of fluid through a flexible tube, the flexible tube providing fluid communication between a fluid source and a patient, the system comprising:

a transparent plate mounting the flexible tube at a first surface of the transparent plate, the plate mounting the tube such that the tube has a first level of contact with the first surface when in a normal condition during which fluid is flowing through the tube, a second level of contact with the first surface which is greater than the first level of contact when there exists a downstream blockage of the fluid, and no contact with the first surface when there exists an upstream blockage of the fluid;

a light source disposed for projecting light onto a second surface of the plate in the direction of the first surface and the mounted tube, the second surface spaced from the first surface;

an optical sensor disposed such that it is directed at the second surface of the transparent plate and at the first surface and the tube and is configured to measure reflected light; and means for determining whether measurements of reflected light received from the optical sensor indicate an upstream blockage in flow through the tube or a downstream blockage.

12. The system of claim 11 wherein the means for determining includes an electronic synchronizer.

13. The system of claim 12 wherein the electronic synchronizer further comprises:

an analog to digital signal converter connected to the optical sensor;

a set of reference values stored electronically; and a comparator which receives digital signals from the signal converter and receives the stored reference values.

14. The system of claim 11 further comprising:

an alarm configured to activate in response to adverse indications from the means for determining.

15. The system of claim 11 wherein the second surface of the transparent plate has a first recess which forms a lens configured to direct light emitted from the light source onto the first surface, and the second surface of the transparent plate has a second recess which forms a lens configured to direct light reflected from the first surface into the optical sensor.

16. A system for detecting deviations in the flow of fluid through a flexible tube, the flexible tube providing fluid communication between a fluid source and a patient, the system comprising:

a transparent plate in contact with the tube;

a light source for projecting light onto the plate; and an optical sensor directed at the transparent plate for measuring reflected light;

wherein the said plate having a first recess at which the light source is directed and a second recess at which the optical sensor is directed, each recess having a lens for directing light.

17. A system for detecting blockages in the flow through a tube comprising:

a flexible tube providing fluid communication between a fluid source and a patient, said tube defining a first diameter under a reference state due to a uniform rate of flow through the tube;

a transparent plate in contact with the tube while the tube is in the reference state; and a light source configured to project light onto the transparent plate; and an optical sensor configured to measure the light reflected from the transparent plate.

18. The system of claim 17 further comprising:

an electronic comparator configured to receive signals from the optical sensor and determine whether the tube has deviated from the reference state.

19. The system of claim 18 wherein the electronic comparator determines whether the tube is in an expanded state due to a downstream blockage or a contracted state due to an upstream blockage.

20. The system of claim 18 wherein the electronic comparator further determines the presence of an air bubble in the tube.

* * * * *